(12) United States Patent
Castor

(10) Patent No.: US 8,637,074 B2
(45) Date of Patent: Jan. 28, 2014

(54) METHODS FOR CO-ENCAPSULATION OF COMBINATION DRUGS AND CO-ENCAPSULATED COMBINATION DRUG PRODUCT

(75) Inventor: Trevor Percival Castor, Arlington, MA (US)

(73) Assignee: Aphios Corporation, Woburn, MA (US)

( * ) Notice: Subject to any disclaimer, the term of this patent is extended or adjusted under 35 U.S.C. 154(b) by 468 days.

(21) Appl. No.: 12/384,007

(22) Filed: Mar. 31, 2009

(65) Prior Publication Data

US 2010/0247620 A1    Sep. 30, 2010

(51) Int. Cl.
*A61K 9/127* (2006.01)
*A61P 35/00* (2006.01)

(52) U.S. Cl.
USPC ........................................... 424/450

(58) Field of Classification Search
None
See application file for complete search history.

(56) References Cited

U.S. PATENT DOCUMENTS 5,554,382 A * 9/1996 Castor ........................... 424/450
2006/0228300 A1* 10/2006 Chang et al. .................. 424/1.49
2008/0107722 A1* 5/2008 Tardi et al. .................... 424/450

FOREIGN PATENT DOCUMENTS

WO    WO 2010009186 A1 *  1/2010

OTHER PUBLICATIONS

Castor, T., Current Drug Delivery, 2005, 2, 329-340.*
Dexheimer et al. Anticancer Agents Med Chem. May 2008 ; 8(4): 381-389.*

* cited by examiner

*Primary Examiner* — Janet Epps-Smith
(74) *Attorney, Agent, or Firm* — Lathrop & Gage LLP; Anthony J. Janiuk

(57) ABSTRACT

This invention is for an improved process to co-encapsulate hydrophobic drugs and hydrophilic drugs in phospholipid liposomes. Non-toxic supercritical or near-critical fluids with/without polar cosolvents are utilized to solubilize phospholipid materials and hydrophobic drugs, and form uniform liposomes to encapsulate hydrophobic drugs and hydrophilic drugs.

21 Claims, 2 Drawing Sheets

METHODS FOR CO-ENCAPSULATION OF COMBINATION DRUGS AND CO-ENCAPSULATED COMBINATION DRUG PRODUCT

GOVERNMENT SUPPORT

Research leading to this invention was in part funded with the Contract No. HHSN-2612008000-26C from the National Cancer Institute, National Institutes of Health, Bethesda, Md., USA.

FIELD OF THE INVENTION

This invention relates to methods for co-encapsulating two or more drugs for use in combination therapy. The methods relate to improving the drug delivery of therapeutics and other products, and to making more effective and less toxic combination drugs for cancers and other medical diseases. The methods feature supercritical, critical and near-critical fluids with and without polar cosolvents.

BACKGROUND OF THE INVENTION

DNA topoisomerase I (Top1) is ubiquitous and essential in higher eukaryotes. It relieves DNA torsional stress and relaxes DNA supercoiling by introducing DNA single-strand breaks, which are produced by the covalent linking of the Top1 catalytic tyrosine residue (Y723 in humans) to a 3'-DNA phosphate. Thus, these breaks are referred to as "Top1 cleavage complexes". Once the DNA is relaxed, each break is religated as the 5'-end of the broken DNA reseals the break by attacking the phosphotyrosyl bond, which releases Top1. Top1-DNA cleavage complexes are normally undetectable because they are very transient.

Top1 cleavage complexes can selectively be trapped by the natural alkaloid camptothecin (Hsiang et al., 1985) as the drug binds at the enzyme-DNA interface and prevents DNA religation. Two camptothecin derivatives are used in cancer therapy [topotecan (Hycamtin; GlaxoSmithKline, Uxbridge, Middlesex, UK) and irinotecan (CPT-11, Camptosar; Pfizer, New York, N.Y.)], and several families of non-camptothecin inhibitors are being developed as novel anticancer agents. Top1 cleavage complexes can also be trapped by endogenous DNA lesions, including abasic sites, mismatches, oxidized bases, nicks, and carcinogenic DNA adducts. Hence, DNA modifications such as those associated with oxidative damage (thousands per cell per day) can stabilize Top1 cleavage complexes. In contrast to camptothecins and other Top1 inhibitory drugs, these DNA modifications produce irreversible cleavage complexes when the 5'-end of the DNA is irreversibly misaligned, as in the case of abasic sites or DNA breaks. The irreversible cleavage complexes are commonly referred to as "suicide complexes." Reversible cleavage complexes trapped by drugs can also be converted into irreversible complexes after collision of replication forks or transcription complexes with the Top1 cleavage complexes.

Tyrosyl-DNA phosphodiesterase (Tdp1) was discovered as an enzyme that specifically removes the 3'-phosphotyrosyl adducts. Top1 needs to be proteolyzed or denatured for Tdp1 to hydrolyze the tyrosyl-DNA bond. Top1 degradation and ubiquitination have indeed been observed after camptothecin treatment.

Tdp1 orthologs are present in all eukaryotic species examined, including yeasts and humans. Sequence comparisons and structural studies revealed that Tdp1 is a member of the phospholipase D (PLD) superfamily, which also includes a bacterial toxin, poxvirus envelope proteins, and bacterial nucleases.

In humans, homozygous mutation in the TDP1 gene (1478A-G) resulting in substitution of histine 493 with arginine is responsible for "spinocerebellar ataxia with axonal neuropathy" (SCAN1). Recent studies demonstrated that SCAN1 cells are hypersensitive to camptothecin and that Tdp1 is required for the repair of abortive Top1 cleavage complexes. Tdp1 forms multiprotein complexes with the single-strand break repair XRCC1 complexes by direct interaction with DNA ligase III. These complexes are catalytically defective in SCAN1 cell extracts, which accumulate Tdp1-DNA intermediates. Tdp1 can also remove glycolate residues from the 3'-end of DNA. 3'-Phosphoglycolate is a common byproduct of DNA double-strand breaks caused by oxidative fragmentation of DNA sugars, which occur as a result of ionizing radiation and oxidative DNA damage. Consistently, extracts from SCAN1 cells are deficient in processing 3'-phosphoglycolate. Thus, Tdp1 seems to repair Top1-DNA adducts and free-radical-mediated DNA breaks. Because the latter can also generate Top1 covalent complexes, Top1 repair is probably a critical function of Tdp1.

In budding yeast, a T722A mutant Top1 that induces high level of cleavage complexes by increasing their stability results in low viability. However, Tdp1 deficiency alone does not confer hypersensitivity to Top1 cleavage complexes unless an additional mutation of the RAD9 checkpoint gene or the RAD1 endonuclease gene is associated with a TDP1-null mutation. Moreover, Tdp1 overexpression in human cells counteracts DNA damage mediated not only by Top1 but also by Top2. Because cancer cells are characteristically defective in checkpoint and DNA repair, and oncogenic transformation produces high levels of oxidative radicals, it is plausible that Tdp1 inhibitors might be used for anticancer treatment alone or more likely in combination with camptothecins or other Top1 inhibitors.

Just recently, aminoglycosides and other antibiotic ribosome inhibitors were reported as the first pharmacological inhibitors for Tdp1. The only other inhibitors of Tdp1 are vanadate and tungstate, which are general inhibitors of a variety of enzymes involved in phosphoryl transfer reactions. Using recombinant human Tdp1 and model tyrosyl-oligonucleotides substrates, it has been shown that antibiotics that target bacterial ribosomes can inhibit Tdp1 activity. Potential Tdp1 inhibitors are neomycin and tetracycline.

The development of Tdp1 inhibitors as anticancer agents can be envisioned as combinations of Tdp1 and Top1 inhibitors. Tumor cells, whose repair pathways are commonly deficient, might be selectively sensitized to Top1 inhibitors compared with normal cells that contain redundant repair pathways. Moreover, Tdp1 inhibitors might also be effective by themselves as anticancer agents because oncogenic activation tends to increase free radical production and genomic instability. In addition, Tdp1 inhibitors might be valuable as anti-infectious agents because the gene is present in parasites.

Aspects of the present invention employ materials known as supercritical, critical or near-critical fluids. A material becomes a critical fluid at conditions which equal its critical temperature and critical pressure. A material becomes a supercritical fluid at conditions which equal or exceed both its critical temperature and critical pressure. The parameters of critical temperature and critical pressure are intrinsic thermodynamic properties of all sufficiently stable pure compounds and mixtures. Carbon dioxide, for example, becomes a supercritical fluid at conditions which equal or exceed its critical temperature of 31.1° C. and its critical pressure of 72.8 atm (1,070 psig). In the supercritical fluid region, normally gaseous substances such as carbon dioxide become dense phase fluids which have been observed to exhibit greatly enhanced solvating power. At a pressure of 3,000 psig (204 atm) and a temperature of 40° C., carbon dioxide has a density of approximately 0.8 g/cc and behaves much like a nonpolar organic solvent, having a dipole moment of zero Debyes.

A supercritical fluid displays a wide spectrum of solvation power as its density is strongly dependent upon temperature and pressure. Temperature changes of tens of degrees or pressure changes by tens of atmospheres can change a compound solubility in a supercritical fluid by an order of magnitude or more. This feature allows for the fine-tuning of solvation power and the fractionation of mixed solutes. The selectivity of nonpolar supercritical fluid solvents can also be enhanced by addition of compounds known as modifiers (also referred to as entrainers or cosolvents). These modifiers are typically somewhat polar organic solvents such as acetone, ethanol, methanol, methylene chloride or ethyl acetate. Varying the proportion of modifier allows wide latitude in the variation of solvent power.

In addition to their unique solubilization characteristics, supercritical fluids possess other physicochemical properties which add to their attractiveness as solvents. They can exhibit liquid-like density yet still retain gas-like properties of high diffusivity and low viscosity. The latter increases mass transfer rates, significantly reducing processing times. Additionally, the ultra-low surface tension of supercritical fluids allows facile penetration into microporous materials, increasing extraction efficiency and overall yields.

A material at conditions that border its supercritical state will have properties that are similar to those of the substance in the supercritical state. These so-called "near-critical" fluids are also useful for the practice of this invention. For the purposes of this invention, a near-critical fluid is defined as a fluid which is (a) at a temperature between its critical temperature ($T_c$) and 75% of its critical temperature and at a pressure at least 75% of its critical pressure, or (b) at a pressure between its critical pressure ($P_c$) and 75% of its critical pressure and at a temperature at least 75% of its critical temperature. In this definition, pressure and temperature are defined on absolute scales, e.g., Kelvin and psia. To simplify the terminology, materials which are utilized under conditions which are supercritical, near-critical, or exactly at their critical point will jointly be referred to as "SCCNC" fluids or referred to as "SFS."

SCCNC fluids can be used for the co-encapsulation of the hydrophobic Top1 inhibitor (camptothecins) and the hydrophilic Tdp1 inhibitor (antibiotics) in phospholipid nanosomes (small, uniform liposomes). Camptothecins are quite hydrophobic and will be packaged in the lipid bilayer. Antibiotics such as tetracycline and neomycin are quite water-soluble and will be packaged in the aqueous core of phospholipid nanosomes.

The nanosomal formulation of the co-encapsulated drugs will result in reduced systemic toxicity, due to the masking of the cytotoxic effects of camptothecins and Tdp1 inhibitors. Additionally, the stability of the lactone ring in the nanosomes will be improved as a result of protection from the neutral pH of the blood stream. By increasing residence time in the circulatory system, the nanosomes increase therapeutic efficacy of the combination drugs. Optionally, pegylated phospholipids will be utilized to provide steric hindrance that will further increase residence time and therapeutic efficacy as is done with Doxil® liposome encapsulated doxorubicin. Furthermore, phospholipids linked with specific antibodies or ligands will be utilized to target the co-encapsulated camptothecin and Tdp1 inhibitor to specific cancers in the colon, lung or ovary. Such smart targeting will further reduce toxicities associated with both Top1 and Tdp1 inhibitors while increasing efficacy and therapeutic index.

At present, there are no available technologies that can readily co-encapsulate hydrophobic and hydrophilic drugs in phospholipid nanosomes in a single step, scalable process. Conventional processes for the encapsulation of hydrophobic drugs utilize many processing steps and require large quantities of organic solvents. These processes are very time consuming, costly and inefficient. Generally, such phospholipid liposomes have a wide dispersion of particle size. Such phospholipid liposomes tend to have a median size greater than 100 microns in diameter. In addition, the exposure of therapeutic agent to the organic solvent may adversely affect the integrity of the final product. Other conventional processes for the encapsulation of hydrophilic drugs into phospholipid liposomes utilize high pressure homogenization that requires a significant amount of recycling, generates heat with every pass through the homogenizer, and could be contaminated with heavy metal particles. These conventional processing methods may also compromise sterility, or do not provide sterility.

Embodiments of the present invention address these problems inherent in the prior art with the application of supercritical, critical or near-critical fluids with or without a cosolvent or modifier.

SUMMARY OF THE INVENTION

Embodiments of the present invention are directed to methods of using supercritical fluids for co-encapsulating hydrophobic and hydrophilic drugs in phospholipid liposomes. The uniformity and integrity of such liposomes make such liposomes ideal for containing therapeutic drugs such as Top1 inhibitors, Tdp1 inhibitors and other products. The methods require reduced processing steps, time and preparation costs.

One embodiment of the present invention is a method of making phospholipid nanosomes comprising the steps of providing a phospholipid and hydrophobic drug solution of these materials dissolved in a first fluid. The first fluid consisting of a supercritical, critical or near-critical fluid with or without a cosolvent or modifier. Next, the phospholipid and hydrophobic drug solution is depressurized as said phospholipid and hydrophobic drug solution exits one or more orifices in the presence of a low solubility fluid containing a hydrophilic drug. The low solubility fluid has low volatility and the phospholipid and hydrophobic drug materials are in concentrations which exceed the solubility of the phospholipid and hydrophobic materials in the low solubility fluid. The phospholipid and hydrophobic drug materials form liposomes containing the hydrophobic drug and the hydrophilic drug, and the first fluid is removed during depressurization.

Embodiments of the present invention feature the formation of liposomes having an average diameter of between 0.01 and 10.0 microns and, most preferably, 0.1 and 1.0 microns. The narrow range of diameter of the liposomes that can be attained with the present method is unusual and surprising.

Preferably, the phospholipid and hydrophobic drug solution is depressurized to ambient pressure.

A preferred phospholipid is selected from one or more of the group of synthetic and derivatized phospholipids, including phosphatidylcholine (PC), phosphatidylglycerol (PG), phosph-atidylserine (PS), dimyristoylphosphatidylcholine (DMPC), dimyristoylphosphatidylglycerol (DMPG), phosphatidylethanolamine (PE) and polyethylene conjugated distearylphosph-atidylethanolamine (either DSPE-PEG$_{2000}$ or DSPE-PEG$_{3500}$) and α-tocopherol (vitamin E), a common non-toxic dietary lipid, as an anti-oxidant. The phospholipid may contain specific antibodies or ligands for specific cancers in the colon, lung, brain or ovary.

Preferred first fluids comprise propane, fluorohydrocarbons, nitrous oxide, ethylene, ethane and carbon dioxide. The first fluid may also contain cosolvents or modifiers. Preferred modifiers are ethanol, methanol, propanol, butanol, methylene chloride, ethyl acetate and acetone. A preferred temperature and pressure for a SCCNC comprising propane are a temperature in the range of 10 to 60° C. and a pressure in the range of 1,000 to 5,000 psig.

The low solubility fluid, preferably, comprises an aqueous solvent, such as distilled water or a buffer such as PBS. Preferably, the low solubility fluid has a chemical agent such as sucrose for stabilizing the liposomes.

DETAILED DESCRIPTION OF PREFERRED EMBODIMENTS

Figure 1:
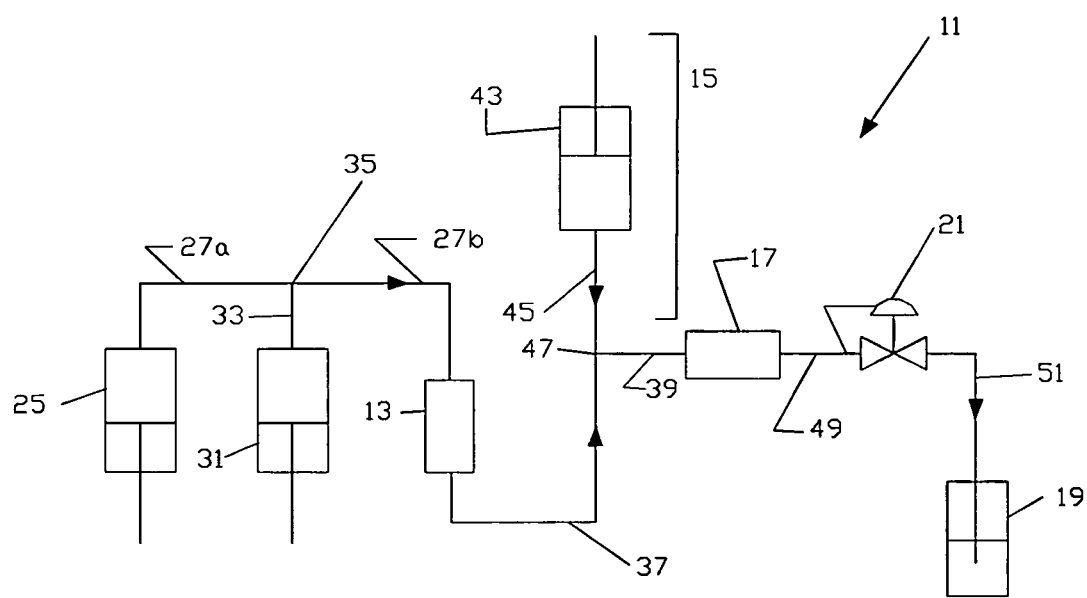
FIG. 1 depicts in schematic form an apparatus embodying features of the present invention.

The present method and apparatus will be described with respect to FIG. 1 which depicts in schematic form a phospholipid liposome apparatus, generally designated by the numeral 11. The phospholipid liposome apparatus is comprised of the following major elements: a phospholipid vessel 13, a hydrophobic drug injection assembly 15, an admixture chamber 17, a depressurization vessel 19, and an orifice nozzle 21.

Phospholipid vessel 13 is in fluid communication with a SCCNC syringe pump 25 via conduits 27a and 27b. SCNCC pump 25 is in fluid communication with a source of SCCNC fluid (not shown).

Phospholipid vessel 13 is also in fluid communication with a modifier syringe pump 31 via conduit 33 which intersects with conduit 27a and 27b at junction 35. Modifier syringe pump 31 is in communication with a source of modifiers and/or entrainers (not shown).

Phospholipid vessel 13 is loaded with phospholipid. And, phospholipid vessel receives SCNCC fluid from SCNCC pump 25 via conduits 27a and 27b. Phospholipid vessel 13 receives modifiers and/or entrainers from Modifier pump 31 via conduit 33. Phospholipid is dissolved in the SCNCC fluid and modifier to form a phospholipid solution.

Phospholipid vessel 13 is in fluid communication with admixture chamber 17 via conduits 37 and 39. Admixture chamber 17 is also in fluid communication with hydrophobic drug injection assembly 15. Hydrophobic drug injection assembly 15 comprises hydrophobic drug syringe pump 43, a source of hydrophobic drug material (not shown) and conduit 45. Hydrophobic drug syringe pump 43 is in communication with a source of hydrophobic drug material and pressurizes and compels such material through conduit 45. Conduit 45 is in communication with admixture chamber via conduits 39 which intersects conduit 45 at junction 47. Preferably junction 47 is a mixing "T".

Admixture vessel 17 is in the nature of an inline mixer and thoroughly mixes incoming streams from the phospholipid vessel 13 and hydrophobic drug injection assembly 15. Admixture vessel 17 is in communication with orifice nozzle 21 via conduit 49. Orifice nozzle 21 is in the nature of a back pressure regulator and has a nozzle defining one or more orifices which discharge into depressurization vessel 19 via conduit 51. Preferably orifice nozzle 21 controls pressure and decompression rates.

The operating pressure of the system can be preset at a precise level via a computerized controller (not shown) that is part of the syringe pumps. Temperature control in the system is achieved by enclosing the apparatus 11 in ¼" Lexan sheet while utilizing a Neslab heating/cooling system coupled with a heat exchanger (not shown) to maintain uniform temperature throughout the system.

In a typical experimental run, polymeric materials were first packed into the phospholipid vessel 13. SCCNC and an ethanolic solution of hydrophobic drug were charged into the SCNCC syringe pumps 25 and 31, respectively, and brought to the desired operating pressure. In the alternative, a ethanol solution of hydrophobic drug is charged into bioactive syringe pump 43.

The system was then pressurized with the SCCNC (supercritical fluid (SCF) and cosolvent) via SCNCC syringe pump 25 to the pressure level equal to that set in modifier syringe pump 31 and hydrophobic drug syringe pump 43, and maintained at this level with the nozzle orifice 21. The dynamic operating mode for all pumps was set so that each pump can be operated at its own desired flow rate. The SCCNC stream flowed through the phospholipid vessel 13, dissolved phospholipid and contacted the hydrophobic drug stream at junction 47. The mixture of SCCNC, hydrophobic drug and phospholipid materials was then passed through admixture chamber 17 for further mixing. Finally, the mixed solution entered orifice nozzle 21 and was injected into a 10% sucrose solution containing hydrophilic drug in the depressurization vessel 19. As a result of supercritical fluid decompression, phospholipid liposomes containing hydrophobic drug and hydrophilic drug are formed in the 10% sucrose solution and the expanded supercritical fluid exited the system via a vent line on the depressurization vessel 19.

EXAMPLES

Example 1

Co-Encapsulation of Camptothecin and Neomycin (TDP-10)

TDP-10 was conducted to encapsulate both camptothecin in the lipid bilayer and neomycin in the aqueous core. TDP-10 was performed with SFS propane and 20% ethanol at 3,000 psig and 40° C. in the phospholipid nanosomes apparatus shown in FIG. 1, with a 0.030" injector and 150.0 mL mixing chamber.

In TDP-10, the operational and collection procedures were as follows: circulation time for 20 minutes, then depressurization from ~3,000 psig to atmospheric pressure (0 psig). This operation was repeated twice. Each of the three fractions was collected into 50 mL of 10% sucrose solution at a temperature of 5° C.

The TDP-10 samples were first checked by HPLC for content of camptothecin (CPT) and neomycin, and particle size was measured utilizing a Coulter 4MND sub-micron particle size analyzer. Results for TDP-10 are listed in Table1.

TABLE 1

Camptothecin Content and Size of TDP-10 Phospholipid Nanosomes

| TDP-10 Fraction | Amount of CPT (mg/100 mL) | Amount of Neomycin (mg/100 mL) | Size (nm) |
|---|---|---|---|
| Product 1 | 0.206 | | 141 |
| Product 2 | 0.118 | | 351 |
| Product 3 | 0.106 | | 1870 |

Example 2

Co-Encapsulation of Irinotecan and Tetracycline (TDP-12)

TDP-12 was conducted to encapsulate both irinotecan in the lipid bilayer and tetracycline in the aqueous core. TDP-12 was performed under similar conditions to TDP-10. These conditions were SFS propane with 20% ethanol at 3,000 psig and 40° C. in the SFS phospholipid nanosomes apparatus shown in FIG. 1, with a 0.030" injector and 150.0 mL mixing chamber.

In TDP-12, the operational and collection procedures were as follows: circulation time for 20 minutes, then depressurization from ~3,000 psig to atmospheric pressure (0 psig). This operation was repeated twice. Each of the three fractions was collected into 50 mL of 10% sucrose solution at a temperature of 5° C.

The TDP-12 samples were first checked by HPLC for content of irinotecan and tetracycline content, and particle size was measured utilizing a Coulter 4MND sub-micron particle size analyzer. Results for TDP-12 are listed in Table 2.

TABLE 2

Irinotecan and Tetracycline Content, and Size of TDP-12 Phospholipid Nanosomes

| TDP-12 Fraction | Amount of Irinotecan (mg/100 mL) | Amount of Tetracycline (mg/100 mL) | Size (nm) |
|---|---|---|---|
| Product 1 | 1.823 | 1.277 | 178 |
| Product 2 | 0.461 | 1.242 | 641 |
| Product 3 | 0.164 | 1.282 | 1390 |

Example 3

TDP-12-01 Filtration 20 mL of a 75 mL sample of TDP-12-01 was filtered through a 0.1 μm polycarbonate filter using compressed $N_2$. Between 40-50 psi was used for filtration to occur over about 15 hours. The 16 mL of filtrate collected was checked for irinotecan (Irino) and tetracycline (Tet) content and particle size. Results for the sterile filtration of TDP-12 are listed in Table 3.

TABLE 3

Irinotecan and Tetracycline Content and Size of Filtered TDP-12-01 Phospholipid Nanosomes

| Sample | Tet (mg/mL) | Irino (mg/mL) | Mean Diameter (nm) |
|---|---|---|---|
| TDP-12-1 | 1.278 | 0.201 | 178 |
| TDP-12-1 after 0.1 μm polycarbonate filtration | 1.274 | 0.198 | 544 |

The sample TDP-12-1 that had been filtered allowed almost all of the Irino and tetracycline to pass through. The reduction of compound corresponds to the amount of sample lost (4 mL) during the filtration. The irinotecan and tetracycline did not appear to have degraded during this time frame. The particle size analysis of the filtrates indicates that the nanosomes were larger than prior to filtration, indicating some disruption and reformation during 0.1 μm filtration. Another possible explanation of the increased particle size is the evaporation of ethanol from the formulation and the diffusion of the ethanol out of the nanosomes during the filtration process. The osmotic outward diffusion of ethanol out of the nanosomes could change the fluidity of the lipid membrane and the size of the nanosomes.

Example 4

TDP-12 Size Exclusion

The premise for the separation using Sephadex LH-20 is that during an aqueous elution of a nanosomal preparation of tetracycline/irinotecan that the nanosomes should not be retained by the column and should elute close to the void volume. Any non-encapsulated tetracycline/irinotecan, which is not soluble in water, should adsorb onto the packing material and not elute using water. A methanol flush of the system should release any tetracycline/irinotecan that has adsorbed. HPLC analysis of each fraction should determine how much tetracycline/irinotecan is encapsulated.

Figure 2:
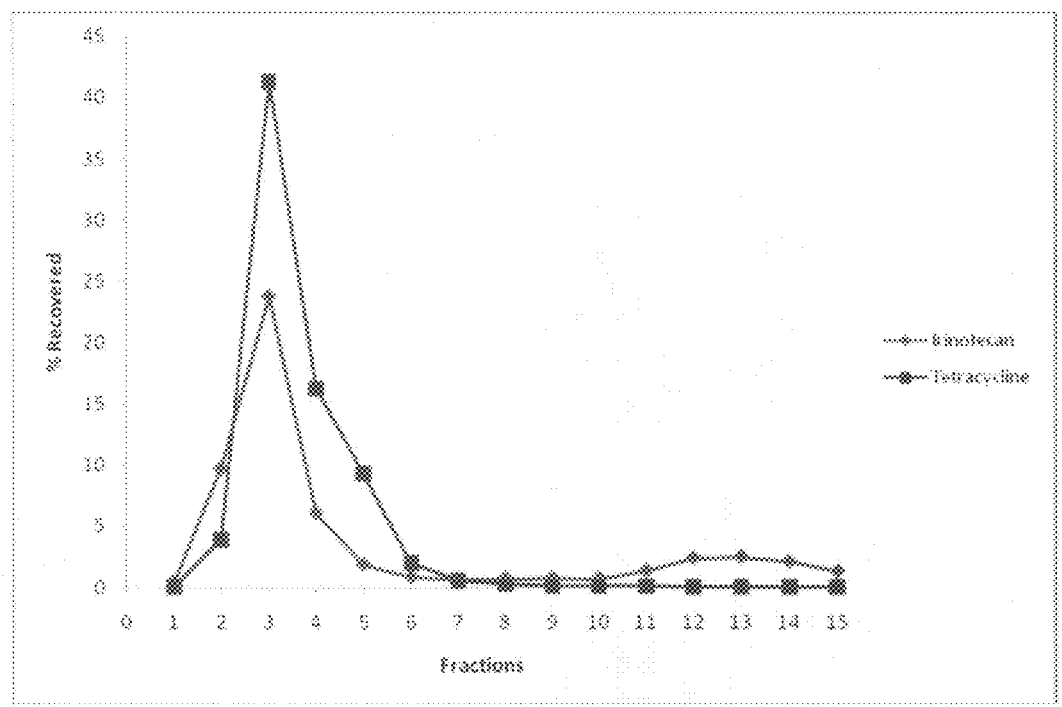
FIG. 2 shows percentage recovery of irinotecan and tetracycline in SEC Fractions of TDP-12-01

Analysis of the SEC fractions are summarized in Table 4 and plotted in FIG. 2.

TABLE 4

Irinotecan and Tetracycline Content as well as Particle Size of SEC Fractions of TDP-12-01

| TDP-12-01 size excl. fraction | Total Irino (mg) | Volume of fraction (mL) | Total Tet (mg) | Particle Size (nm) |
|---|---|---|---|---|
| 1 | 0.004 | 5 | 0 | 131 |
| 2 | 0.095 | 4 | 0.232 | 371 |
| 3 | 0.232 | 4 | 2.467 | 355 |
| 4 | 0.060 | 4 | 0.970 | 254 |
| 5 | 0.018 | 4 | 0.556 | 178 |
| 6 | 0.008 | 4 | 0.119 | 168 |
| 7 | 0.007 | 4 | 0.031 | — |
| 8 | 0.007 | 4 | 0.014 | — |
| 9 | 0.007 | 4 | 0.007 | — |
| 10 | 0.007 | 4 | 0.005 | — |
| 11 | 0.013 | 4 | 0.003 | — |
| 12 | 0.023 | 4 | 0.002 | — |
| 13 | 0.024 | 4 | 0.001 | — |

Example 5

TDP-12-01 Ultracentrifugation 10 mL of a 75 mL sample of TDP-12-01 was filtered using an Amicon Ultra-15 (10,000 MWCO; Cat#: UFC 901024) at ambient temperature and 4,000 rpm. The filtration took ~8 hours to complete. 300 μL of retentate (SN) were recovered and 9.7 mL of filtrate was recovered.

The retentate had 9.7 mL of 10% sucrose added to it to bring the volume back to 10 mL. The filtrate had 300 μL of 10% sucrose added to it to bring the volume back to 10 mL. Both of the samples were checked by HPLC for Irinotecan (Irino) and tetracycline (Tet) as well as particle size. 100 μL of the samples were diluted with 1 mL of 15% ACNB mobile phase to obtain the correct concentration range for analysis.

TABLE 5

Irinotecan and Tetracycline Content, and Particle Size Analyses of Ultracentrifugation Fractions of TDP-12-01

| Sample | Tetracycline (mg/mL) | Irinotecan (mg/mL) | Mean Diameter (nm) |
|---|---|---|---|
| TDP-12-1 | 1.277 | 0.201 | 178 |
| TDP-12-1 Filtrate | 1.351 | 0.211 | 428 |
| TDP-12-1 Retentate | 0.061 | 0.019 | 329 |

Example 6

TDP-12-01 Dialysis

Dialysis tubing (10,000-12,000 MWCO) was washed and equilibrated in DI-H$_2$O for 1 hr. 10 mL of a 75 mL sample of TDP-12-01 was put into the washed dialysis tubing and the system was placed carefully into a beaker containing 150 mL of sterile 10% sucrose W/V and ethanol (50 mL ethanol and 100 mL 10% sucrose). The solution was swirled periodically (ca every 30 min). During the day, the dialysis was set at room temperature (25° C.) and 4° C. at night.

The sucrose diffusate was decanted carefully into an Erlenmeyer flask twice after elapsed times of 42 and 64 hrs. Each time another 150 mL of sterile 10% sucrose and ethanol was added (50 mL ethanol and 100 mL 10% sucrose). The solution was swirled periodically (ca every 30 min). One mL samples of the diffusate were taken at times 0.083, 17, 24, 38.5, 42 (after buffer change), 47, 63, 64, 66 and 69 hours.

After a total elapsed time of 69 hrs the dialysis tubing was removed from the diffusate and the top clip carefully removed. The contents of the dialysis tubing (retentate) were removed using a graduated pipette; 9.8 mL of retentate was recovered. The retentate and diffusate samples were analyzed by HPLC for Irinotecan and Tetracycline as is without further dilution. The results of the dialysis of TDP-12-01 are summarized in Table 6.

TABLE 6

Irinotecan and Tetracycline Content and Particle Size Analyses of Ultracentrifugation Fractions of TDP-12-01

| Sample | Tet (mg/mL) | Irino (mg/mL) | Mean Diameter (nm) |
|---|---|---|---|
| TDP-12-1 | 1.201 | 0.186 | 178 |
| TDP-12-1 Retentate | 0.046 | 0.013 | 151 |
| TDP-12-1 Combined Diffusates | 0.026 | 0.004 | N/A |

The mean diameter of the TDP-12-01 retentate is 151 nm and unimodal, about the same as the TDP-12-01 feed. This result indicates that the increased size of the retentate in the previous dialysis experiment was caused by the diffusion of the ethanol out of the nanosomes because the diffusate was not balanced in ethanol concentration with the retentate.

It is intended that the matter contained in the preceding description be interpreted in an illustrative rather than a limiting sense.

What is claimed is:

1. A method of making phospholipid liposomes having an average diameter of between 0.01 and 10.0 microns, comprising the steps of:
   a.) providing a phospholipid material, hydrophobic drug and a first fluid consisting of a supercritical, critical or near-critical fluid; and, forming a first hydrophobic drug solution of said phospholipid material, hydrophobic drug in said first fluid;
   b.) providing an aqueous solution and a hydrophilic drug and forming a second hydrophilic drug solution;
   c.) depressurizing said first hydrophobic drug solution in the presence of said second hydrophilic drug solution, as said first hydrophobic drug solution exits one or more orifices in the presence of said second hydrophilic drug solution, said phospholipid material, hydrophobic drug, and hydrophilic drug forming phospholipid liposomes having an average diameter between 0.01 and 10.0 microns and said first fluid removed during depressurization.

2. The method of claim 1 wherein said phospholipid liposomes have an average diameter of between 0.1 to 1.0 microns.

3. The method of claim 1 wherein said first hydrophobic drug solution is depressurized to ambient pressure.

4. The method of claim 1 wherein said aqueous solution is selected from the group consisting of de-ionized water, PBS and 10% sucrose solution.

5. The method of claim 1 wherein said phospholipid material is selected from one or more of the group consisting of phosphatidylcholine (PC), phosphatidylglycerol (PG), phosph-atidylserine (PS), dimyristoylphosphatidylcholine (DMPC), dimyristoylphosphatidylglycerol (DMPG), phosphatidylethanolamine (PE) and polyethylene conjugated distearylphosph-atidylethanolamine, α-tocopherol (vitamin E), and derivatives thereof.

6. The method of claim 1 wherein said first hydrophobic solution comprises specific ligands for specific cancers of at least one organ system selected from the group consisting of colon, lung, brain and ovary.

7. The method of claim 1 wherein said first fluids is selected from the group of compounds consisting of propane, fluorohydrocarbons, nitrous oxide, ethylene, ethane and carbon dioxide.

8. The method of claim 7 wherein the first fluid has at least one cosolvents or modifier.

9. The method of claim 8 wherein said first fluid is propane at a temperature in the range of 10 to 60° C. and a pressure in the range of 1,000 to 5,000 psig.

10. The method of claim 1 wherein said hydrophobic drug is a topoisomerase 1 inhibitor.

11. The method of claim 10 wherein said topoisomerase 1 inhibitor is selected from the group consisting of camptothecin, irinotecan, topotecan and derivatives thereof.

12. The method of claim 1 wherein such hydrophilic drug is a tyrosyl-DNA phosphodiesterase (Tdp1) inhibitor.

13. The method of claim 12 wherein said tyrosyl-DNA phosphodiesterase (Tdp1) inhibitor is an aminoglycoside antibiotics.

14. A therapeutic drug product comprising a plurality of spheres having an average diameter of 0.1 to 1.0 microns, said spheres having a phospholipid surface and containing a hydrophobic drug selected from the group consisting of topoisomerase 1 inhibitors and a hydrophilic drug selected from the group consisting of tyrosyl-DNA phosphodiesterase (Tdp 1) inhibitors.

15. The therapeutic drug product of claim 14 wherein said topoisomerase 1 inhibitor is camptothecin, irinotecan, topotecan and derivatives thereof.

16. The therapeutic drug product of claim 14 wherein said tyrosyl-DNA phosphodiesterase (Tdp1) inhibitor is an aminoglycoside antibiotics.

17. The therapeutic drug product of claim 16 wherein said aminoglycoside antibiotics is selected from the group consisting of neomycin, and tetracycline.

18. The therapeutic drug product of claim 14 wherein said tyrosyl-DNA phosphodiesterase (Tdp1) inhibitor is a ribosome inhibitor.

19. The therapeutic drug product of claim 18 wherein said ribosome inhibitor is selected from the group consisting of thiostrepton, clindamycin-2-phosphate, and puromycin.

20. The method of claim 12 wherein said tyrosyl-DNA phosphodiesterase (Tdp1) inhibitor is a ribosome inhibitor.

21. The method of claim 20 wherein said ribosome inhibitor is selected from the group consisting of thiostrepton, clindamycin-2-phosphate, and puromycin.

\* \* \* \* \*